United States Patent
Ying et al.

(10) Patent No.: US 10,031,133 B2
(45) Date of Patent: Jul. 24, 2018

(54) BIOLOGICAL SAMPLE SIGNAL AMPLIFICATION METHOD USING BOTH TERAHERTZ METAMATERIALS AND GOLD NANOPARTICLES

(71) Applicant: ZHEJIANG UNIVERSITY, Hangzhou (CN)

(72) Inventors: Yibin Ying, Hangzhou (CN); Wendao Xu, Hangzhou (CN); Lijuan Xie, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 86 days.

(21) Appl. No.: 15/106,710

(22) PCT Filed: Jul. 17, 2015

(86) PCT No.: PCT/CN2015/084344
§ 371 (c)(1),
(2) Date: Jun. 20, 2016

(87) PCT Pub. No.: WO2017/011940
PCT Pub. Date: Jan. 26, 2017

(65) Prior Publication Data
US 2017/0205403 A1    Jul. 20, 2017

(51) Int. Cl.
*G01N 33/543* (2006.01)
*G01N 21/3586* (2014.01)
(Continued)

(52) U.S. Cl.
CPC ....... *G01N 33/54306* (2013.01); *C12Q 1/682* (2013.01); *G01N 21/3586* (2013.01); *G01N 33/54346* (2013.01); *G01N 33/553* (2013.01)

(58) Field of Classification Search
CPC ..... G01N 33/54306; C12Q 1/68; C12M 1/00; C40B 30/04
See application file for complete search history.

(56) References Cited

U.S. PATENT DOCUMENTS 7,368,280 B2 * 5/2008 Zhang .............. G01N 33/54373
422/417

OTHER PUBLICATIONS

Wu et al , Alkanethiol-functionalized terahertz metamaterial as label-free, highly-sensitive and specific biosensor, 2013, Biosensors and Bioelectronics, 42, 626-631. (Year: 2013).*

(Continued)

*Primary Examiner* — Narayan Bhat
(74) *Attorney, Agent, or Firm* — Tian IP & Technology, LLC.

(57) ABSTRACT

Implementations herein relates to a biological sample signal amplification method using terahertz metamaterials and gold nanoparticles. A plurality of biological sample solutions and a plurality of gold nanoparticles-labeled avidin solutions are dropped on surfaces of metamaterials and dried at room temperature. Terahertz time-domain signals of sample points and reference sample points on the surfaces of metamaterials are acquired, transmission or reflectance of the sample points and the reference sample points are calculated using terahertz time-domain signals, and the frequency shift of transmission or reflection peaks are calculated according to the lowest point of transmission or reflectance. The effect of local electric field enhancement of metamaterials is used for sample signal amplification, gold nanoparticles are used to change a distribution of electric fields, and a sample signal is further enhanced by gold nanoparticles modification.

13 Claims, 4 Drawing Sheets

(51) Int. Cl.
    *G01N 33/553*    (2006.01)
    *C12Q 1/682*    (2018.01)

(56) References Cited

OTHER PUBLICATIONS

Xie et al, Extraordinary sensitivity enhancement by metasurfaces in terahertz detection of antibiotics, 2015, Scientific Reports, 5, 8671, pp. 1-4, (Year: 2015).*

Xu et al, Gold Nanoparticle-Based Terahertz Metamaterial Sensors: Mechanisms and Applications, 2016, ACS photonics, 3, 2308-2314. (Year: 2016).*

\* cited by examiner

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: synthesized

<400> SEQUENCE: 1
tatcctgaga ccgcgttttt ttttt                                          25
```

BIOLOGICAL SAMPLE SIGNAL AMPLIFICATION METHOD USING BOTH TERAHERTZ METAMATERIALS AND GOLD NANOPARTICLES

CROSS REFERENCE TO RELATED APPLICATION

This application is a national stage application of International application number PCT/CN2015/084344, filed Jul. 17, 2015, titled "Biological sample signal amplification method using both terahertz metamaterials and gold nanoparticles", which is hereby incorporated by reference in its entirety.

TECHNICAL FIELD

The present disclosure relates to a terahertz signal amplification method of biological sample, and more particularly, to a biological sample signal amplification method using both terahertz metamaterials and gold nanoparticles.

SEQUENCE LISTING

The Sequence Listing associated with this application is provided in text format in lieu of a paper copy and is hereby incorporated by reference into the specification. The name of the text file containing the Sequence Listing is Sequence_listing.txt, which was generated on Jan. 8, 2018.

BACKGROUND

With the development of detection technology, spectroscopy techniques gradually attract wide attention from domestic and foreign scholars due to their fast and easy operations. Terahertz spectroscopy, as a new spectroscopic technique, gradually attracts people's attention. Some vibrational and rotational energy of macromolecules fall in terahertz bands; so terahertz wave is considered to be a very promising method of biological sample detection. For some fields of terahertz spectroscopy techniques with large prospects, such as security, biology, medicine, agriculture and materials characterization, etc., trace amounts of ultrafine NDT is in need in those fields. However, due to disadvantages including low energy terahertz source and limited direct detection sensitivity, it is difficult for terahertz technology to be used in rapid detection of trace amount samples.

SUMMARY

In order to overcome the disadvantages in the prior art above, the present disclosure provides a biological sample signal amplification method using both terahertz metamaterials and gold nanoparticles, which is highly sensitive, easy and fast.

The technical solution adopted in the present disclosure is as below.

1) Provide a plurality of biological sample solutions with different concentrations and a plurality of gold nanoparticles-labeled avidin solutions with different concentrations;

2) Drop biological sample solution on a surface of metamaterials: dropping the biological sample solutions on one surface of the cleaned metamaterials, dropping at least three times with each concentration, and randomly setting three reference sample points, reference sample points are different from the sample points to be measured, and then drying the metamaterials at room temperature as FIG. 2 illustrated;

3) Drop gold nanoparticles-labeled avidin solutions on a surface of metamaterials: dropping the gold nanoparticles-labeled avidin solutions on one surface of another cleaned metamaterials, dropping at least three times with each concentration, and randomly setting three reference sample points, reference sample points are different from the sample points to be measured, and then drying the metamaterials at room temperature as FIG. 2 illustrates;

4) Collect terahertz time-domain signals of all the sample points and reference sample points on the surface of metamaterials: placing the biological samples on the sample point to be measured in nitrogen atmosphere, and collecting the terahertz time-domain signals of all the sample points to be measured and the reference sample points on the surface of metamaterials within the 0.1-3.5 THz spectral bandwidth;

5) Obtain the frequency shift of a transmission peak or a reflection peak from the terahertz time-domain signals: calculating the transmittance or reflectance of all the sample points and the reference sample points, the frequencies with lowest value of sample's curve and reference's curve are used for frequency shift calculation: converting the terahertz time-domain signal of biological samples to the frequency-domain signal using fast Fourier transform, calculating the transmittance or reflectance of reference sample points by the frequency-domain signal, calculating the absolute value of the difference of lowest value of transmittance or reflectance between reference sample points and the sample points to be measured, which is used as the frequency shift of the transmission peak or the reflection peak to achieve the signal amplification of avidin detection.

In the step 2) and 3), the metamaterials may be cleaned by the following operations: taking a piece of complete terahertz metamaterials, cleaning it using deionized water, then phosphate buffer and, deionized water again, and drying it with nitrogen gas.

In the step 1), the gold nanoparticle-labeled avidin solution is provided in the following operations.

1.1) Preserve the mixed raw materials: mixing ordinary avidin and gold nanoparticles, the mixed molar ratio of ordinary avidin and gold nanoparticles is from 10:1 to 2500:1, as shown in FIG. 1, oscillating it in a shaker in room temperature, and then preserving it at $0$~$4°$ C.; the formed solution is a color of wine red;

1.2) Extraction of gold nanoparticles-labeled avidin: obtaining the gold nanoparticles-labeled avidin and placing it into a centrifuge tube, after centrifuging in the centrifuge, removing excess supernatant ordinary avidin in the centrifuge tube, cleaning the precipitate using deionized water repeatedly, then adding deionized water and thoroughly oscillating to obtain the gold nanoparticles-labeled avidin solutions.

In the step 1.2), the speed of centrifugation in the centrifuge is 5000~15000 rpm, and the centrifugal time is 10 to 20 minutes.

In the step 4), the detection area of sample point to be measured is greater than 1 mm$^2$ when collecting terahertz time-domain signal.

The biological sample includes ordinary avidin, DNA and/or *Escherichia coli*.

In the step 1), the concentrations of the gold nanoparticles-labeled avidin solutions and the biological sample solutions are ranging from $2 \times 10^{-10}$ to $10 \times 10^{-10}$ mol/L.

In the step 3) or step 4), volumes of the biological sample solutions or the gold nanoparticles-labeled avidin solutions dropped at a time are from 5 to 100 μL.

The biological sample is DNA or *Escherichia coli*, and the plurality of gold nanoparticles-labeled avidin solutions with different concentrations are a complex of biological sample solutions and gold nanoparticles-labeled avidin solutions.

The method and process of compositions are provided as follow: gold nanoparticles-labeled avidin can specifically bind to biotin-labeled biological sample, forming the complex solutions of gold nanoparticles-labeled avidin and biotin-labeled biological samples, and the concentration ratio of gold nanoparticles-labeled avidin and biotin or biological sample is at least 1:1, preferably 1: 1-4:1.

In the step 1.1), the pH of ordinary avidin is 5~9, and the pH of gold nanoparticles is 8~12.

In the step 4), the humidity is less than 0.2% when collecting terahertz time-domain signal using this terahertz time-domain spectroscopy.

The ordinary avidin in the implementations of the present disclosure can preferably be Sigma company's avidin with an item number A9275, but it is not limited to this.

The particle size of gold nanoparticles is 8-90 nm.

The gold nanoparticles-labeled avidin in the present disclosure can be used in a biotin-avidin binding reaction, so this signal amplification method has wide applications in DNA hybridization and antigen-antibody reaction.

The gold nanoparticles in the present disclosure can be directly used in sample signal amplification without excitation of surface plasmons, showing a significant effect of signal amplification.

The gold nanoparticles in the present disclosure can be replaced with other metal nanoparticles, including silver nanoparticles, gold nanorods, gold nanoparticles with silver shell, silver nanoparticles with gold shell etc.

In a particular implementation of the present disclosure, it is preferably to use a terahertz time-domain spectroscopy system produced by z-omega company with a model z3.

The present disclosure employs terahertz time-domain spectroscopy, a new study and detection technology in the international development in recent years. So far, terahertz time-domain spectroscopy technique has been applied in many fields such as national defense, pharmaceutical, chemical, food and materials. Terahertz wave is an electromagnetic wavelength between infrared and microwave radiation with a frequency of 0.1-10 THz. Although the energy of terahertz radiation is very low, a large number of molecules, in particular, many organic macromolecules (DNA, proteins, etc.) show strong absorptions and dispersions in this band.

Metamaterials of the present disclosure are an artificial material produced by a periodic structure, which can exhibit properties that do not exist in many nature materials. In recent years, terahertz metamaterials gradually attracts attention of broad scholars with some applications including communication, absorber and so on. In recent years, metamaterials have gradually been used in terahertz sensing applications.

Thus the present disclosure utilizes terahertz metamaterials technology and has the following beneficial effects.

The present disclosure combines terahertz metamaterials and modification of gold nanoparticles, which can enhance sample signal by the local electric field enhancement effects of metamaterials.

The present disclosure utilizes gold nanoparticles to change the distribution of electric field and further enhances the sample signal by gold nanoparticles modification method, and thus this method is highly sensitive.

Compared with conventional technique by making sample into pellets, this method of the present disclosure can greatly improve the detection sensitivity. Also, this method is simple, rapid, which can meet the growing demand for rapid detection.

Figure 1:
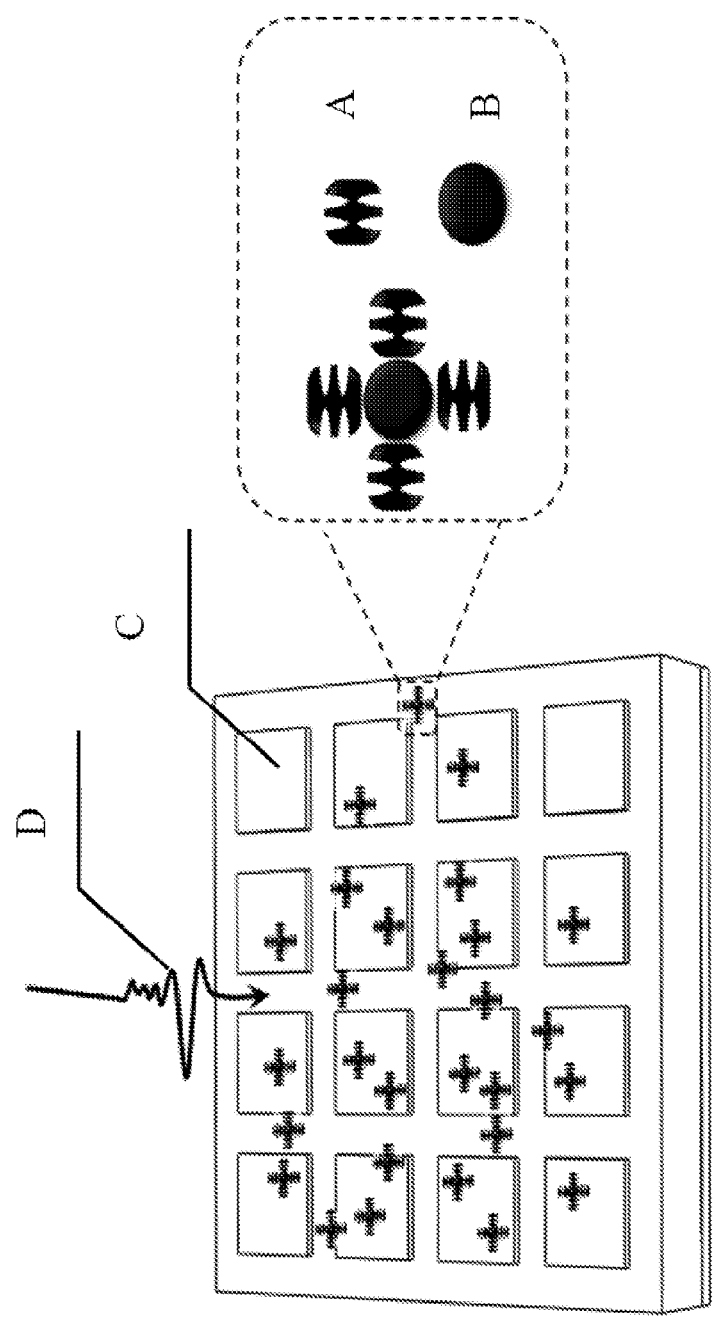
FIG. 1 illustrates schematics of gold nanoparticles-labeled avidin detection using metamaterials in the present disclosure.
Figure 2:
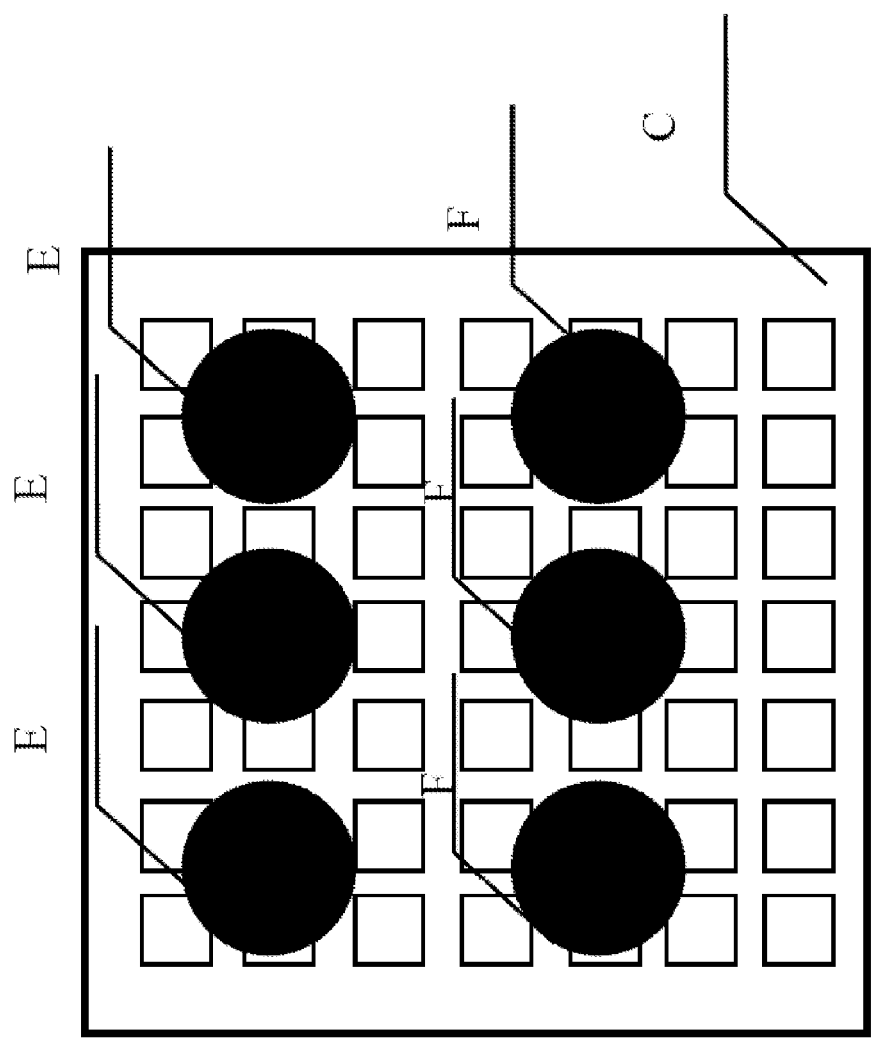
FIG. 2 illustrates of distributions of sample points and reference sample points on surfaces of metamaterials of Embodiment 1 in the present disclosure.

In the Figures above, A represents ordinary avidin, B represents gold nanoparticles, C represents metamaterials, D represents terahertz wave, E represents a sample point, and F represents a reference sample point.

DETAILED DESCRIPTION OF THE PREFERRED EMBODIMENTS

The present disclosure is further detailed by the specific embodiments in combination with the drawings, but the present disclosure is not limited to the following embodiments.

Embodiments of the present disclosure are provided as follows.

Embodiment 1

(1) Clean metamaterials: a piece of complete metamaterials was taken by tweezers, cleaned using deionized water, then phosphate buffer, and deionized water three times, and was dried with nitrogen gas.

(2) Provide gold nanoparticles-labeled avidin: clean gloves were used, 300 μL 1 mg/mL ordinary avidin (pH ~7) was pipetted to a cleaned centrifuge tube, then 0.5 mL 20 nmol/L gold-nanoparticles solution (pH~10) was pipetted before mixing them (the mole ratio of ordinary avidin and gold nanoparticles is approximately 2500:1) and was oscillated for 15 minutes in a shaker at room temperature. The mixture was then stored in the refrigerator at 4° C. for at least 0.5 hour.

(3) Extraction of gold nanoparticles-labeled avidin: the centrifuge tube of gold nanoparticles-labeled avidin was obtained from a refrigerator, an equal amount of deionized water was added into another same centrifuge tube, the two centrifuge tubes were trimmed and centrifuged with a speed of 10000 rpm for 15 minutes. Since extra ordinary avidin is suspended in the upper part and gold nanoparticles-labeled avidin is in the lower part after centrifugation, the supernatant was removed, precipitates were washed with deionized water repeatedly, and the excess ordinary avidin was removed.

(4) Obtain gold nanoparticles-labeled avidin solution: after cleaning the gold nanoparticles-labeled avidin, 500 μL deionized water to the centrifuge tube was added and gold nanoparticles-labeled avidin in deionized water was dissolved by shaking.

(5) Add ordinary avidin solution on the surface of metamaterials: ordinary avidin solution with five concentration gradient (in this embodiment, these concentrations are $2\times10^{-10}$ mol/L, $4\times10^{-10}$ mol/L, $6\times10^{-10}$ mol/L, $8\times10^{-10}$ mol/L and $10\times10^{-10}$ mol/L) were provided, 10 µL of ordinary avidin solution was added onto the surface of clean metamaterials, at least three times with each concentration were dropped, and three reference sample points were randomly set, then the metamaterials were dried at room temperature (the amount of ordinary avidin are 2 fmol, 4 fmol, 6 fmol, 8 fmol, 10 fmol), and the detection area of sample point to be measured is around 4 mm².

(6) Add gold nanoparticles-labeled avidin solution on the surface of metamaterials: gold nanoparticles-labeled avidin solutions with five concentration gradient (in this embodiment, these concentrations are $2\times10^{-10}$ mol/L, $4\times10^{-10}$ mol/L, $6\times10^{-10}$ mol/L, $8\times10^{-10}$ mol/L and $10\times10^{-10}$ mol/L) were provided, 10 µL of gold nanoparticles-labeled avidin solution was added onto the surface of cleaned metamaterials, at least three times with each concentration were dropped, three reference sample points were randomly set, then the metamaterials were dried at room temperature (the amount of ordinary avidin are 2 fmol, 4 fmol, 6 fmol, 8 fmol, 10 fmol), and the detection area of sample point to be measured is around 4 mm².

(7) Collect the terahertz time-domain signal of all the sample points and reference sample points on the metamaterials surface: laser, computer, controller, and nitrogen valve were opened, the humidity is getting lower in the terahertz time-domain spectroscopy system because of the nitrogen pumping, the measurement can be carried out after laser has warm-up for a half-hour, terahertz time-domain spectroscopy measurement system was opened and put the metamaterials in light path using a jig. In a nitrogen atmosphere, the terahertz time-domain signal of all the sample points and reference sample points were collected on the metamaterials surface in the 0.1-3.5 THz region, individually. The ambient humidity should be less than 0.2%, the temperature is room temperature, terahertz time-domain spectroscopy was collected and preserved one by one using the measure method above, and all the terahertz time-domain spectroscopy data of sample points and reference sample points were obtained.

(8) Calculate transmittance or reflectance for all the sample points and find the frequencies with lowest value of transmittance or reflectance: the terahertz time-domain signals of samples were converted to frequency-domain signal using fast Fourier transform, and the transmittance or reflectance curve of sample was calculated using the frequency-domain signals, and transmittance or reflectance can be obtained by the following formula:

$$T = (E_{(sample-T)}/E_{(reference-T)})^2$$

$$R = (E_{(sample-R)}/E_{(reference-R)})^2.$$

In the above formulas, T represents transmittance, $E_{(sample-T)}$ represents the electric field intensity of the sample points in transmission mode, $E_{(reference-T)}$ represents the electric field intensity of the reference sample points in transmission mode, R represents the reflectance, $E_{(sample-R)}$ represents the electric field intensity of the sample point in reflection mode, and $E_{(reference-R)}$ represents the electric field intensity of the reference sample points in reflection mode.

Figure 3:
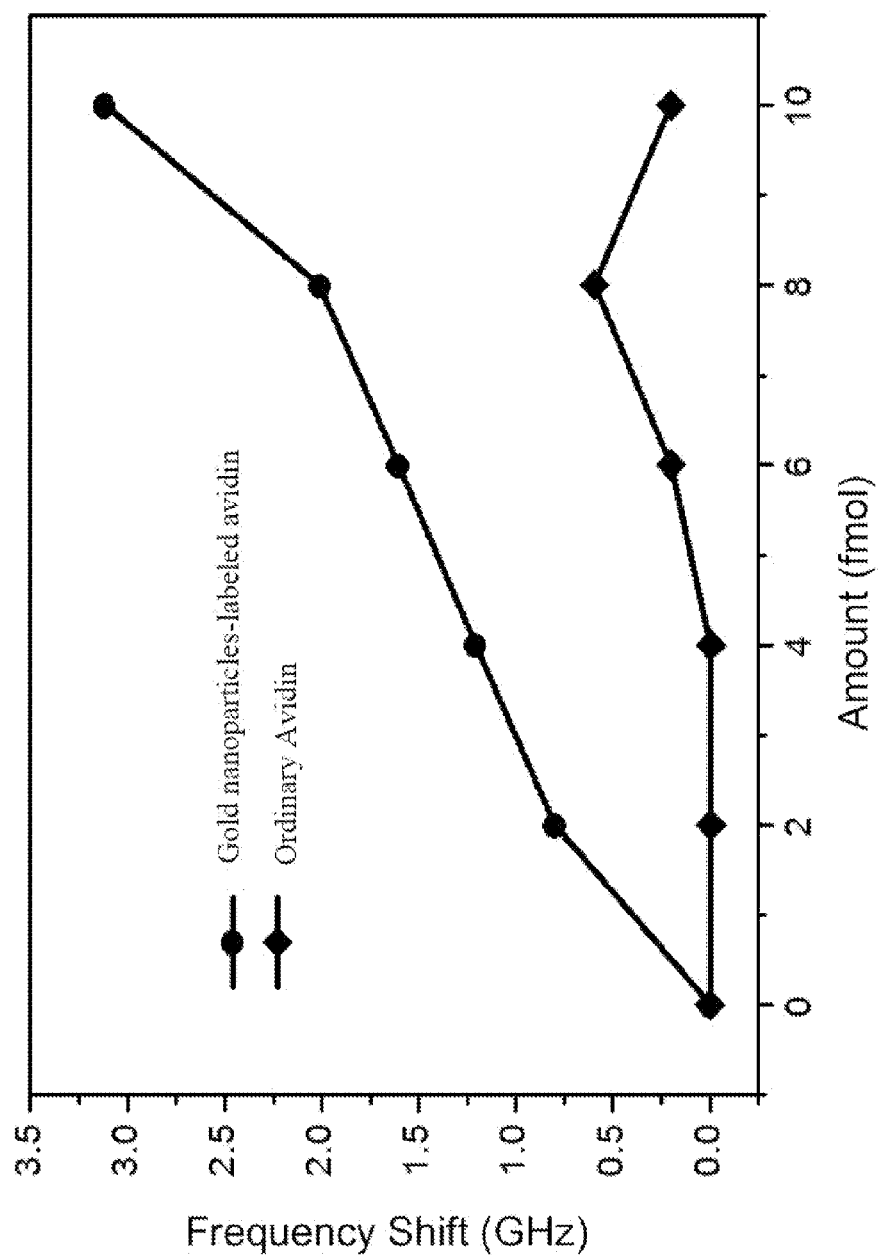
FIG. 3 illustrates a resonant frequency shift of terahertz metamaterials caused by ordinary avidin and gold nanoparticles-labeled avidin of Embodiment 1 in the present disclosure.

The frequency with lowest value of transmittance or reflectance were found, frequencies of sample points from reference sample point was subtracted to obtain the peak frequency shift of transmittance or reflectance, as shown in FIG. 3.

Embodiment 2

(1) Clean metamaterials: a piece of complete metamaterials was taken using tweezers, cleaned using deionized water, then phosphate buffer, and using deionized water three times, and it was dried with nitrogen gas.

(2) Provide gold nanoparticles-labeled avidin: clean gloves were used, 300 µL 0.8 mg/mL ordinary avidin (pH⁻5) was pipetted to a cleaned centrifuge tube, then 0.5 mL 20 nmol/L gold-nanoparticles solution (pH⁻9) was pipetted to mix them (the mole ratio of ordinary avidin and gold nanoparticles is approximately 2000:1) and to oscillate 15 minutes on a shaker at room temperature, and the mixture was stored in the refrigerator at 0° C. for at least 0.5 hour.

(3) Extraction of gold nanoparticles-labeled avidin: gold nanoparticles-labeled avidin was obtained from the refrigerator, an equal amount of deionized water was added into another same centrifuge tube, two centrifuge tubes were trimmed and centrifuged with a speed of 15000 rpm for 10 minutes. After centrifugation, extra ordinary avidin is suspended in the upper part, gold nanoparticles-labeled avidin was in the lower part, the supernatant was removed, precipitates were washed with deionized water repeatedly to remove the excess ordinary avidin.

(4) Obtain gold nanoparticles-labeled avidin solution: after cleaning the gold nanoparticles-labeled avidin, 500 µL deionized water was added to the centrifuge tube, and gold nanoparticles-labeled avidin was dissolved in deionized water by shaking.

(5) The binding of gold nanoparticles-labeled avidin and biotinylated target DNA: a centrifuge tube was used to contain the DNA, add PBS buffer and the concentration of DNA solution is 6 µmol/L. Target biotinylated DNA sequences of the present embodiment was provided as follow:

5'-TATCCTGAGACCGCGTTTTTTTTTT-C6-Biotin-3', which can be synthesized by Shenggong (SEQ ID NO: 1).

500 µL of DNA solution was pipetted and added to the gold nanoparticles-labeled avidin for 3 hours' reaction, an equal amount of deionized water was added into another same centrifuge tube, two centrifuge tubes were trimmed and centrifuged with a speed of 5000 rpm for 20 minutes. After centrifugation, excess biotinylated target DNA was suspended in the upper part and the complex of gold nanoparticles-labeled avidin and biotinylated target DNA was determined in the lower part centrifuge tube, the supernatant removed, and sedimentation repeatedly was washed with deionized water, excess biotinylated target DNA was washed and removed, and 0.5 mL of deionized water was added to obtain the complex of gold nanoparticles-labeled avidin and biotinylated target DNA by shaking.

Target biotinylated DNA sequences of the present embodiment is:

5'-TATCCTGAGACCGCGTTTTTTTTTT-C6-Biotin-3', the target biotinylated DNA sequence of actual operation is not limited to this sequence (SEQ ID NO: 1).

(6) Add target DNA solution on the surface of metamaterials: target DNA sequences of the present embodiment is: 5'-TATCCTGAGACCGCGTTTTTTTTTT-C6-3' (SEQ ID NO: 1), target DNA solution with some concentration gradient (in this embodiment, these concentrations are $2\times10^{-10}$ mol/L, $4\times10^{-10}$ mol/L, $6\times10^{-10}$ mol/L, $8\times10^{-10}$ mol/L and $10\times10^{-10}$ mol/L) was provided, 5 µL of target DNA solution was added onto the surface of cleaned metamaterials, at least three times with each concentration were dropped, and three reference sample points were randomly set (without any sample), then the metamaterials were dried at room temperature, and the detection area of the sample point to be measured is around 1 mm².

(7) Add complex of gold nanoparticles-labeled avidin and biotinylated target DNA on the surface of metamaterials: a complex of gold nanoparticles-labeled avidin and biotinylated target DNA with five concentration gradient (in this embodiment, these concentrations are $2\times10^{-10}$ mol/L, $4\times10^{-10}$ mol/L, $6\times10^{-10}$ mol/L, $8\times10^{-10}$ mol/L and $10\times10^{-10}$ mol/L) was provided, 5 μL of complex of gold nanoparticles-labeled avidin and biotinylated target DNA were added onto the surface of cleaned metamaterials, at least three times with each concentration were dropped, and three reference sample points (without any sample) were randomly set, then the metamaterials at room temperature was dried, and the detection area of the sample point to be measured is around 1 mm².

(8) Collect the terahertz time-domain signal of all the sample points and reference sample points on the surface of metamaterials: laser, computer, controller, and nitrogen valve were opened, the humidity is getting lower in the terahertz time-domain spectroscopy system because of the nitrogen pumping, the measurement can be carried out after laser has warm-up for a half-hour, a terahertz time-domain spectroscopy measurement system was opened and the metamaterials were placed in light path using a jig, in a nitrogen pumping atmosphere, the terahertz time-domain signals of all the sample points and reference sample points on the metamaterials surface were collected in the 0.1-3.5 THz region, individually. The ambient humidity should be less than 0.2%, the temperature is room temperature; terahertz time-domain spectroscopy was collected and stored one by one using the measure method above to obtain all the terahertz time-domain spectroscopy data of sample points and reference sample points.

(9) Calculate transmittance or reflectance for all the sample points and find the frequencies with lowest value of transmittance or reflectance: the terahertz time-domain signals of samples to frequency-domain signal were converted using fast Fourier transform, and the transmittance or reflectance curve of sample was calculated using the frequency-domain signals. The frequency with lowest value of transmittance or reflectance was determined and frequencies of sample points from reference sample point was subtracted to obtain the peak frequency shift of transmittance or reflectance.

Embodiment 3

(1) Clean metamaterials: a piece complete metamaterials was taken using tweezers, cleaned using deionized water, then phosphate buffer, and deionized water again before drying using nitrogen gas.

(2) Provide gold nanoparticles-labeled *Escherichia coli* antibody: clean gloves were used, 2 μL 1 mg/mL *Escherichia coli* antibody (pH ~9) was pipetted to a cleaned centrifuge tube, then 0.5 mL 20 nmol/L gold-nanoparticles solution (pH ~8) was pipetted before mixing them (the mole ratio of *Escherichia coli* antibody and gold nanoparticles is approximately 10:1) and oscillated for 15 minutes on a shaker at room temperature.

(3) Extraction of gold nanoparticles-labeled *Escherichia coli* antibody: the centrifuge tube of gold nanoparticles-labeled *Escherichia coli* antibody was removed from the refrigerator, an equal amount of deionized water was added into another same centrifuge tube, the two centrifuge tubes were trimmed and centrifuged with a speed of 5000 rpm for 20 minutes. After centrifugation, the supernatant was removed, and precipitates were washed with deionized water repeatedly.

(4) Obtain gold nanoparticles-labeled *Escherichia coli* antibody solution: after cleaning the gold nanoparticles-labeled *Escherichia coli* antibody, 500 μL deionized water to the centrifuge tube was added, and gold nanoparticles-labeled *Escherichia coli* antibody in deionized water was dissolved by shaking.

(5) Gold nanoparticles-labeled *Escherichia coli* antibody capture *Escherichia coli*: 0.1 mL $10^8$ CFU/mL *Escherichia coli* solution was added to the gold nanoparticles-labeled *Escherichia coli* antibody solution for 2 hours' reaction to obtain complex of gold nanoparticles-labeled *Escherichia coli* antibody and *Escherichia coli*.

(6) Add *Escherichia coli* solution on the surface of metamaterials: *Escherichia coli* solution with five concentration gradient (in this embodiment, these concentrations are $2*10^6$ CFU/mL, $4*10^6$ CFU/mL, $6*10^6$ CFU/mL, $8*10^6$ CFU/mL and $10^7$ CFU/mL) were provided, 100 μL of *Escherichia coli* solution was added onto the surface of clean metamaterials, at least three times with each concentration were dropped, and three reference sample points (without any sample) were randomly set, then the metamaterials was dried at room temperature, and the detection area of the sample point to be measured is over 10 mm².

(7) Add complex of gold nanoparticles-labeled *Escherichia coli* antibody and *Escherichia coli* solution as in the Step 5 on the surface of metamaterials: a complex of gold nanoparticles-labeled *Escherichia coli* antibody and *Escherichia coli* with five concentration gradient (in this embodiment, these concentrations are $2*10^6$ CFU/mL, $4*10^6$ CFU/mL, $6*10^6$ CFU/mL, $8*10^6$ CFU/mL and $10^7$ CFU/mL) was provided, 100 μL of *Escherichia coli* solution was added onto the surface of cleaned metamaterials, at least three times with each concentration were dropped, and three reference sample points (without any sample) were randomly set, then the metamaterials was dried at room temperature, and the detection area of the sample point to be measured is over 10 mm².

(8) Collect the terahertz time-domain signal of all the sample points and reference sample points on the surface of metamaterials: laser, computer, controller, and nitrogen valve were opened, the humidity is getting lower in the terahertz time-domain spectroscopy system because of the nitrogen pumping, the measurement can be carried out after laser has warm-up for a half-hour, terahertz time-domain spectroscopy measurement system was opened and the metamaterials were placed in light path using a jig, in a nitrogen pumping atmosphere, the terahertz time-domain signals were collected of all the sample points and reference sample points on the metamaterials surface in the 0.1-3.5 THz region, individually. The ambient humidity should be less than 0.2%, the temperature is room temperature, and terahertz time-domain spectroscopy was collected and preserved one by one using the measure method above to obtain all the terahertz time-domain spectroscopy data of sample points and reference sample points.

(9) Calculate transmittance or reflectance for all the sample points and find the frequencies with lowest value of transmittance or reflectance: the terahertz time-domain signals of samples to frequency-domain signal were converted using fast Fourier transform, and the transmittance or reflectance curve of sample by the frequency-domain signal was calculated. The frequency with lowest value of transmittance or reflectance was determined, and frequencies of sample points were subtracted from reference sample point to obtain the peak frequency shift of transmittance or reflectance.

Figure 4:
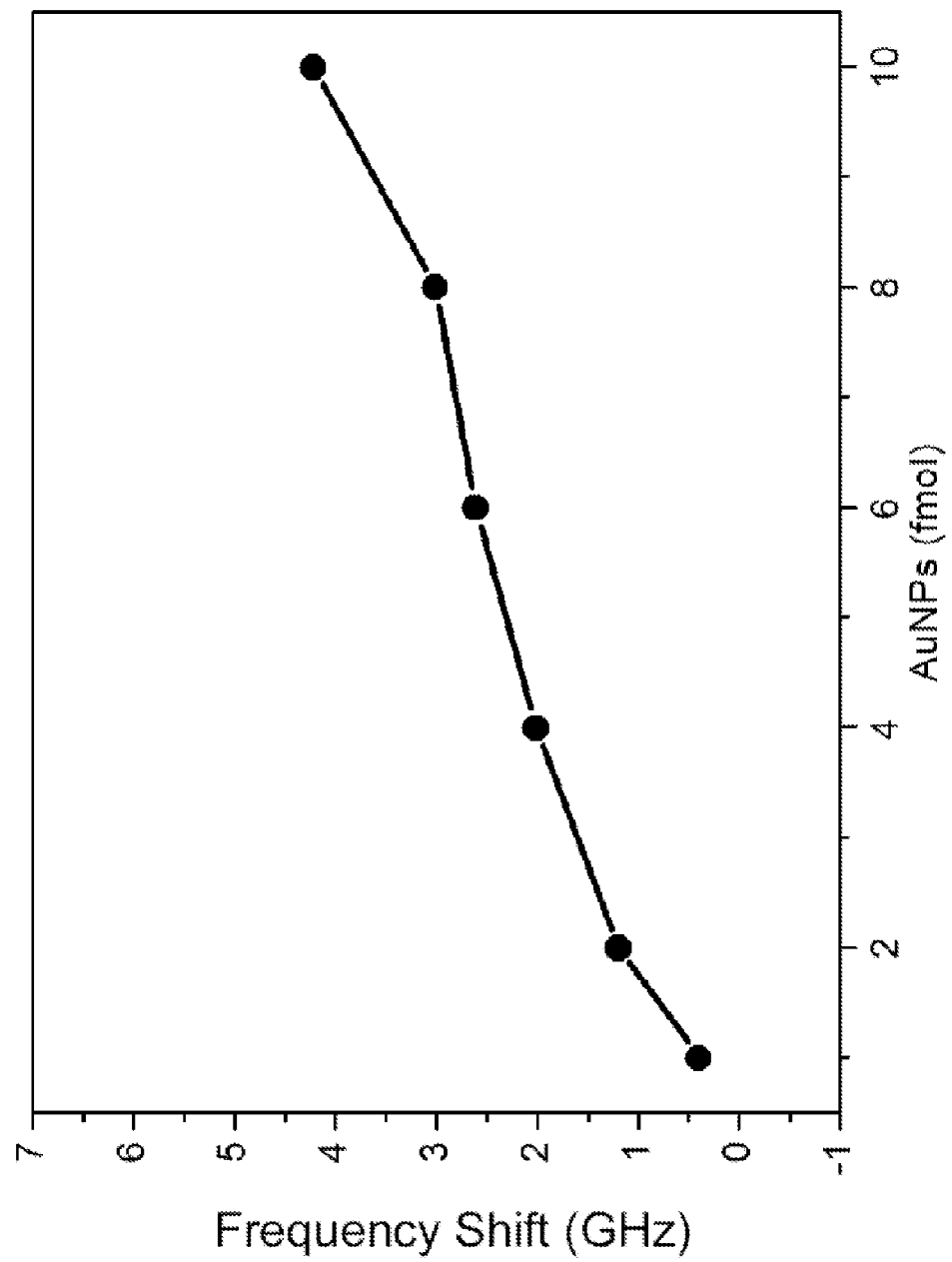
FIG. 4 illustrates a resonant frequency shift of terahertz metamaterials caused by gold nanoparticles of Embodiment 3 in the present disclosure.

As shown in FIG. 4, significant peak frequency shift of metamaterials can be caused by some femtomole of gold nanoparticles. Thus, when linking gold nanoparticles to avidin, DNA or *Escherichia coli*, they can be detected as long as the amount of gold nanoparticles are in femtomole level.

The embodiments above are for describing the present disclosure and not intended to limit the present disclosure. Any modification and changes can be made to the present disclosure without deviating from the spirit and protection scope claimed in the claims, and these modifications and changes are covered by the protection scope of the present disclosure.

---

---

What is claimed is:

1. A method for amplifying signals of biological samples using terahertz metamaterials and gold nanoparticles, the method comprising:

1) providing a plurality of biological sample solutions with different concentrations and a plurality of gold nanoparticles-labeled avidin solutions with different concentrations, wherein each of the biological sample solutions comprises the biological samples each comprising an affinity reagent binding to gold nanoparticles-labeled avidin of the plurality of gold nanoparticles-labeled avidin solutions;

2) contacting the plurality of biological sample solutions with sample points to be measured on a first surface of metamaterials by:

dropping the plurality of biological sample solutions on the first surface of the metamaterials, randomly setting three reference sample points on the first surface of the metamaterials, and drying the first surface of the metamaterials at a room temperature, wherein the reference sample points on the first surface of the metamaterials are different from the sample points to be measured on the first surface of the metamaterials;

3) contacting the plurality of gold nanoparticles-labeled avidin solutions with the sample points to be measured on a second surface of the metamaterials by:

dropping the plurality of gold nanoparticles-labeled avidin solutions on the second surface of the metamaterials, randomly setting three reference sample points on the second surface of the metamaterials, and drying the second surface of the metamaterials at a room temperature, wherein the reference sample points on the second surface of the metamaterials are different from the sample points to be measured on the second surface of the metamaterials;

4) collecting terahertz time-domain signals of the sample points to be measured and the reference sample points on the first and second surfaces of the metamaterials by:

placing the plurality of biological samples on corresponding sample points to be measured in nitrogen atmosphere, and collecting the terahertz time-domain signals of the sample points to be measured and the reference sample points on each of surfaces of the metamaterials within 0.1- to 3.5 THz spectral bandwidth;

5) obtaining a frequency shift of a transmission peak or a reflection peak from the terahertz time-domain signals by:

converting the terahertz time-domain signals of the biological samples to frequency-domain signals using fast Fourier transform, calculating transmittance or reflectance of the reference sample points by the frequency-domain signals, and calculating an absolute value of difference of lowest value of transmittance or reflectance between the reference sample points and the sample points to be measured to perform signal amplification of the biological samples associated with avidin using the frequency shift of the transmission peak or the reflection peak.

2. The method of claim 1, further comprising:

providing the terahertz metamaterials;

cleaning the piece using deionized water, a phosphate buffer, and then deionized water in an order; and drying the piece with nitrogen gas.

3. The method of claim 1, wherein the providing the plurality of gold nanoparticles-labeled avidin solutions with the different concentrations of the gold nanoparticles-labeled avidin comprises:

1.1) mixing an avidin and gold nanoparticles, oscillating in a shaker in room temperature, and preserving the mixed raw materials of the gold nanoparticles-labeled avidin at 0 to 4° C.; and 1.2) obtaining the plurality of gold nanoparticles-labeled avidin solutions by:

extracting the gold nanoparticles-labeled avidin and placing the gold nanoparticles-labeled avidin into a centrifuge tube, removing excess supernatant of the ordinary avidin in the centrifuge tube after centrifugation, cleaning precipitates using deionized water repeatedly, and adding deionized water and oscillating thoroughly to obtain the plurality of gold nanoparticles-labeled avidin solutions.

4. The method of claim 3, wherein a mixed molar ratio of the avidin and the gold nanoparticles is from 10:−1 to 2500:−1.

5. The method of in claim 3, wherein a speed of the centrifugation is 5000 to 15000 rpm, and a centrifugal time is from 10 to 20 minutes.

6. The method of claim 3, wherein a pH value of the avidin is 5 to 9, and a pH value of the gold nanoparticles is 8 to 10.

7. The method of claim 1, wherein a detection area of sample points to be measured is greater than 1 mm$^2$ during collection of the terahertz time-domain signals.

8. The method of claim 1, wherein the biological samples comprises avidin, DNA or *Escherichia coli*.

9. The method of claim 1, wherein a range of the different concentrations of the plurality of gold nanoparticles-labeled avidin solutions is from $2\times10^{-10}$ to $10\times10^{-10}$ mol/L.

10. The method of claim 1, wherein a range of the different concentrations of the plurality of biological sample solutions is from $2\times10^{-10}$ to $10\times10^{-10}$ mol/L.

11. The method of claim 1, wherein a range of volumes of the plurality of biological sample solutions or the plurality of gold nanoparticles-labeled avidin solutions that are dropped on the metamaterials is from 5 to 100 μL.

12. The method of claim 1, wherein humidity of a collection environment is less than 0.2% for collection of the terahertz time-domain signals.

13. The method of claim 1, wherein the biological samples comprises DNA or *Escherichia coli*, the plurality of gold nanoparticles-labeled avidin solutions with different concentrations are a complex of biological sample solutions and gold nanoparticles-labeled avidin solutions.

* * * * *